United States Patent
Chokshi (10) Patent No.: US 8,822,208 B2
(45) Date of Patent: Sep. 2, 2014

(54) BIOREACTOR AND METHOD

(71) Applicant: Becton, Dickinson and Company, Franklin Lakes, NJ (US)

(72) Inventor: Bunkim Chokshi, Cockeysville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/851,536

(22) Filed: Mar. 27, 2013

(65) Prior Publication Data

US 2013/0210132 A1      Aug. 15, 2013

Related U.S. Application Data

(63) Continuation of application No. 11/461,838, filed on Aug. 2, 2006, now abandoned.

(51) Int. Cl.
| | |
|---|---|
| C12M 1/26 | (2006.01) |
| C12M 1/00 | (2006.01) |
| C12M 1/02 | (2006.01) |
| C12M 1/06 | (2006.01) |
| C12M 1/24 | (2006.01) |

(52) U.S. Cl.
CPC ............. *C12M 33/14* (2013.01); *C12M 29/06* (2013.01); *C12M 41/22* (2013.01); *C12M 27/02* (2013.01); *C12M 23/08* (2013.01)
USPC .................. 435/289.1; 435/294.1; 435/296.1; 435/297.1; 435/297.2; 435/297.3; 435/288.6; 435/288.7

(58) Field of Classification Search
CPC ...... C12M 23/08; C12M 27/02; C12M 29/06; C12M 29/04; C12M 33/14; C12M 41/22
USPC .......... 435/289.1, 294.1, 296.1, 297.1, 297.2, 435/297.3, 288.6, 288.7, 303.1, 303.5
See application file for complete search history.

(56) References Cited

U.S. PATENT DOCUMENTS

| | | | | |
|---|---|---|---|---|
| 3,647,632 | A | * | 3/1972 | Johnson ..................... 435/297.3 |
| 3,793,154 | A | | 2/1974 | Efthymiou |
| 4,596,779 | A | | 6/1986 | Ono |
| 4,713,345 | A | | 12/1987 | Ramsden |
| 5,081,036 | A | | 1/1992 | Familletti |
| 5,501,971 | A | | 3/1996 | Freedman et al. |
| 6,455,306 | B1 | * | 9/2002 | Goldstein et al. ............. 435/372 |
| 7,137,974 | B2 | | 11/2006 | Almasian et al. |
| 7,160,442 | B2 | | 1/2007 | Horng et al. |
| 2004/0223405 | A1 | | 11/2004 | Mott |
| 2008/0274539 | A1 | | 11/2008 | Ahluwalia et al. |

* cited by examiner

*Primary Examiner* — Michael Marcheschi
*Assistant Examiner* — Shanta G Doe
(74) *Attorney, Agent, or Firm* — Lerner, David, Littenberg, Krumholz & Mentlik, LLP (57) ABSTRACT

The bioreactor is for use in performing biological and/or biochemical reactions and includes a vessel, an agitator, a reaction assembly, and a harvesting outlet. The vessel of the bioreactor includes several ports including a mixing port, a reaction port, and a harvesting port. The agitator extends through the mixing port into the vessel while the harvesting outlet extends through the harvesting port and permits the withdrawal of reaction medium to another vessel. The reaction assembly extends through the reaction port into the vessel and has multiple components including a gas conduit adapted to introduce gas into a reaction medium in the vessel, a sampling device adapted to remove a portion of the reaction medium from the vessel without contamination of the remaining reaction medium, and an introduction conduit permitting the introduction of at least the reaction medium into the vessel.

17 Claims, 3 Drawing Sheets

BIOREACTOR AND METHOD

CROSS-REFERENCE TO RELATED APPLICATIONS

This application is a continuation of U.S. application Ser. No. 11/461,838, filed on Aug. 2, 2006, now abandoned, the disclosure of which is incorporated herein by reference.

BACKGROUND OF THE INVENTION

The present invention relates to bioreactors for performing biological and/or biochemical reactions. More specifically, the present invention relates to a bioreactor for culturing cells (e.g., biological samples) and for use in the production of medical materials such as hormones, enzymes, antibodies, vaccines, and drugs. The invention further relates to an improved bioreactor that is easy to assemble and maintains sterility throughout the culturing/fermentation operation, and provides for sterile transfer of material to larger vessels.

In the medical field, it is often necessary to cultivate biological samples for further study of cell structures. Such culturing is often carried out in a bioreactor, which is essentially a sterile vessel that provides internal sealed conditions suitable for cell growth. Bioreactors are also used in the production of medical materials such as hormones, enzymes, antibodies, vaccines, and drugs. Typically, the bioreactor produces batch quantities of the desired material to "seed" larger vessels for further processing. These larger vessels are essentially large bioreactors, which continue the culturing/production process. The "smaller" bioreactors are used to produce an effective amount of material of sufficient concentration such that the material can continue culturing/fermentation in the larger vessel. The larger bioreactor vessels have the increased capacity necessary to produce increased quantities of the desired material for study purposes or for further processing into a final product such as a vaccine or drug. The smaller bioreactors, which feed larger vessels, are limited in production capability because, for a given amount of reaction medium introduced into the smaller bioreactor, the bioreactor can generate only a finite amount of product. As a result, transfer of a "seed" product to a larger vessel is necessary for further production.

Generally, three basic types of bioreactors are used in the medical field for producing biological and/or biochemical reactions, namely, a stationary type, a shaking type, and a rotating type. In stationary bioreactors, a fixedly settled reaction vessel, such as an Erlenmeyer flask, is employed in which a stirrer is provided and which operates to produce a generally horizontal rotary movement to cause agitation of the reaction mixture. This stirring action increases the heat transfer and oxygen transfer rate. While this type of bioreactor permits economical running of reactions, it typically cannot operate with a highly viscous substrate due to insufficient driving torque of the stirrer, and the heat and oxygen transfer are mass transfer limited. In this type of bioreactor, substrates with densities different from that of the solvent, (i.e., the reaction medium), tend to float up or settle down which causes separation of the reaction mixture.

In shaking type bioreactors, a shaking culture using test tubes as the culture vessel has been widely used in the medical field. In this type of system, the reaction is accelerated by reciprocating horizontal movement of the culture vessel. This type of bioreactor also does not operate well with highly viscous mediums and also suffers the same mass transfer and separation problems as the stationary type bioreactor discussed previously.

Rotating type bioreactors are most commonly used in the medical field. In rotating bioreactors, the reaction medium is subjected to agitation by a rotating apparatus inserted into the vessel. An example of a rotating bioreactor is disclosed in U.S. Pat. No. 5,587,298 to Horigane et al. This patent discloses a bioreactor comprised of a reaction vessel defining a reaction chamber which is surrounded by a water jacket for maintaining a predetermined constant temperature. The reaction chamber is provided in the vicinity of the inner wall surface of the reaction vessel. A pair of upright screws is disposed in a side-by-side and adjoining relationship and is used to agitate the reaction mixture. In particular, each screw has a screw thread or a helical fin which engages the corresponding screw thread on the adjacent screw to introduce agitation into the reaction mixture. The reaction mixture is subjected to uniform agitation and to a milling and sieving action in the area where the screw threads are engaged.

Another example of a rotating bioreactor is disclosed in U.S. Pat. No. 4,636,675 to Freedman et al. This patent discloses, in particular, an improved agitator for a bioreactor vessel. The agitator includes a hollow body assembly having an open end and a closed end and a tubular structure communicating with the hollow body assembly at a location spaced from the open end. The tubular structure has an exit opening oriented such that rotational movement of the agitator and the tubular structure causes a suction or draft at the exit opening to cause flow of fluid from the open end of the hollow body assembly through the hollow body assembly and out through the tubular structure exit opening. The agitator is driven by a magnetic drive motor.

Another example of a rotating bioreactor is disclosed in U.S. Pat. No. 4,636,675 to Freedman et al. This patent discloses, in particular, an improved agitator for a bioreactor vessel. The agitator includes a hollow body assembly having an open end and a closed end and a tubular structure communicating with the hollow body assembly at a location spaced from the open end. The tubular structure has an exit opening oriented such that rotational movement of the agitator and the tubular structure causes a suction or draft at the exit opening to cause flow of fluid from the open end of the hollow body assembly through the hollow body assembly and out through the tubular structure exit opening. The agitator is driven by a magnetic drive motor.

BRIEF SUMMARY OF THE INVENTION

The bioreactor is intended for use in performing biological and/or biochemical reactions and includes a vessel, an agitator, a reaction assembly, and a harvesting outlet. The vessel of the bioreactor includes several ports including a mixing port, a reaction port, and a harvesting port. The agitator extends through the mixing port into the vessel while the harvesting outlet extends through the harvesting port and permits the withdrawal of reaction medium to another vessel, which may be part of a bioreactor system. The reaction assembly extends through the reaction port into the vessel and has multiple components including a gas conduit adapted to introduce gas into a reaction medium in the vessel, a sampling device adapted to remove a portion of the reaction medium from the vessel without contamination of the remaining reaction medium, and an introduction conduit permitting the introduction of at least the reaction medium into the vessel.

The bioreactor may further include a water jacket adapted to regulate the temperature of the reaction medium. The gas conduit may be adapted to aerate the reaction medium. A sparger may be provided in the gas conduit of the reaction assembly to limit the bubble size of the gas introduced into the vessel. The agitator may extend through a cover sealing the mixing port. The agitator may be adapted to be coupled to an external drive device, for example, a motor.

The sampling device may comprise a collection conduit extending into the vessel, a sampling valve positioned in the collection conduit and disposed outside the vessel, and an extractor associated with the collection conduit and disposed outside of the vessel. The extractor may be adapted to remove a sample portion of reaction medium through the collection conduit. A discharge outlet may be provided for releasing the sample portion of reaction medium from the collection conduit outside of the vessel without contamination of the remaining reaction medium. The extractor may further comprise a vacuum generating portion adapted to decrease pressurization in the collection conduit, and a filter element provided fluidly between the vacuum generating portion and the collection conduit.

The bioreactor may be used as part of a bioreactor system for performing biological and/or biochemical reactions. In such a system, the system includes a seed bioreactor comprising a vessel, an agitator, a reaction assembly, and a harvesting outlet. The vessel of the bioreactor includes several ports including a mixing port, a reaction port, and a harvesting port. The agitator extends through the mixing port into the vessel while the harvesting outlet extends through the harvesting port and permits the withdrawal of reaction medium. The reaction assembly extends through the reaction port into the vessel and has multiple components including a gas conduit adapted to introduce gas into a reaction medium in the vessel, a sampling device adapted to remove a portion of the reaction medium from the vessel without contamination of the remaining reaction medium, and an introduction conduit permitting the introduction of at least the reaction medium into the vessel. The seed bioreactor may be used to "seed" a main (e.g., larger) bioreactor with reaction medium for continuing the biological and/or biochemical reaction process. Such a main bioreactor is adapted to be placed in fluid communication with the vessel via the harvesting outlet and typically includes an inlet port. The main bioreactor may be placed in fluid communication with the vessel via a sanitary connection between the harvesting outlet and the inlet port.

Another aspect of the invention is related to a method of assembling a bioreactor adapted to perform biological and/or biochemical reactions. The method includes providing a vessel comprising a mixing port, a reaction port, and a harvesting port; inserting an agitator into the vessel through the mixing port, with the agitator adapted to stir a reaction medium in the vessel; sealing the mixing port with a cover, with the agitator extending through the cover; sealing the reaction port with a reaction assembly extending through the reaction port and into the vessel; and sealing the harvesting port with a harvesting outlet adapted to permit the sterile withdrawal and transfer of reaction medium to another vessel. The reaction assembly generally comprises a gas conduit adapted to introduce gas into the vessel, a sampling device adapted to remove a portion of the reaction medium from the vessel without contamination of the remaining reaction medium, and an introduction conduit permitting the introduction of at least the reaction medium into the vessel.

A further aspect of the invention relates to a method of preparing biological and/or biochemical reactants, generally comprising the steps of providing a seed bioreactor comprising a vessel having a mixing port, a reaction port, and a harvesting port. The method further includes introducing reactants (i.e., reaction medium) into the vessel through an introduction conduit extending through the reaction port; introducing gas into the reaction medium through a gas conduit extending through the reaction port; agitating the reaction medium with a mixer extending through the mixing port; and transferring at least a portion of the processed reaction medium to a main bioreactor through the harvesting port.

Further details and advantages of the invention will become clear upon reading the following detailed description in conjunction with the accompanying drawing figures, wherein like parts are identified with like reference numerals throughout.

DETAILED DESCRIPTION

For purposes of the description hereinafter, spatial orientation terms, if used, shall relate to an embodiment of the invention as it is oriented in the accompanying drawing figures or otherwise described in the following description of the invention. However, it is to be understood that the invention embodiments described hereinafter may assume many alternative variations and configurations. It is also to be understood that the specific devices illustrated in the accompanying drawing figures and described herein are simply exemplary to the invention and should not be considered as limiting.

Figure 1:
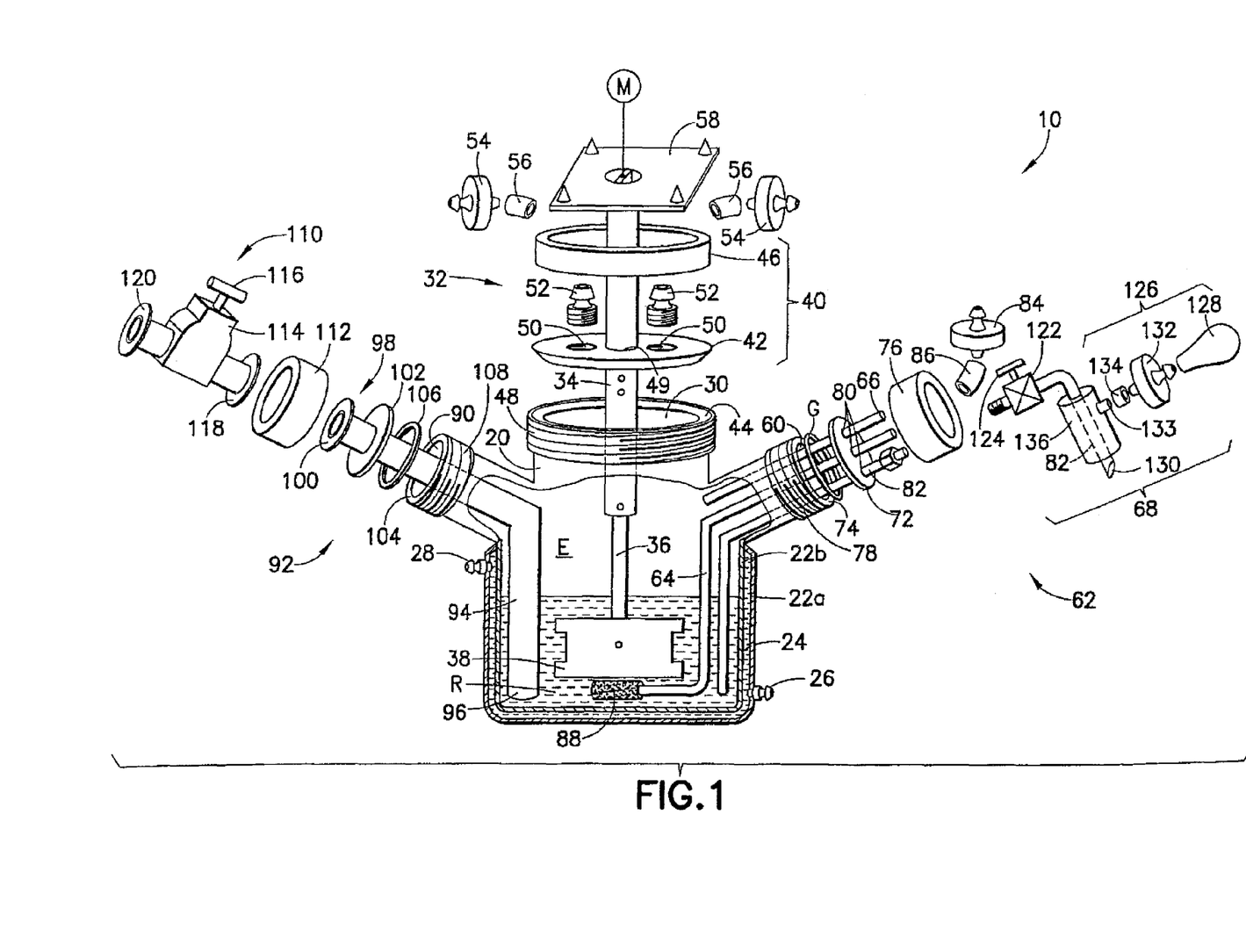
FIG. 1 is an exploded and partially perspective view of a bioreactor pursuant to an embodiment of the present invention.
Figure 2:
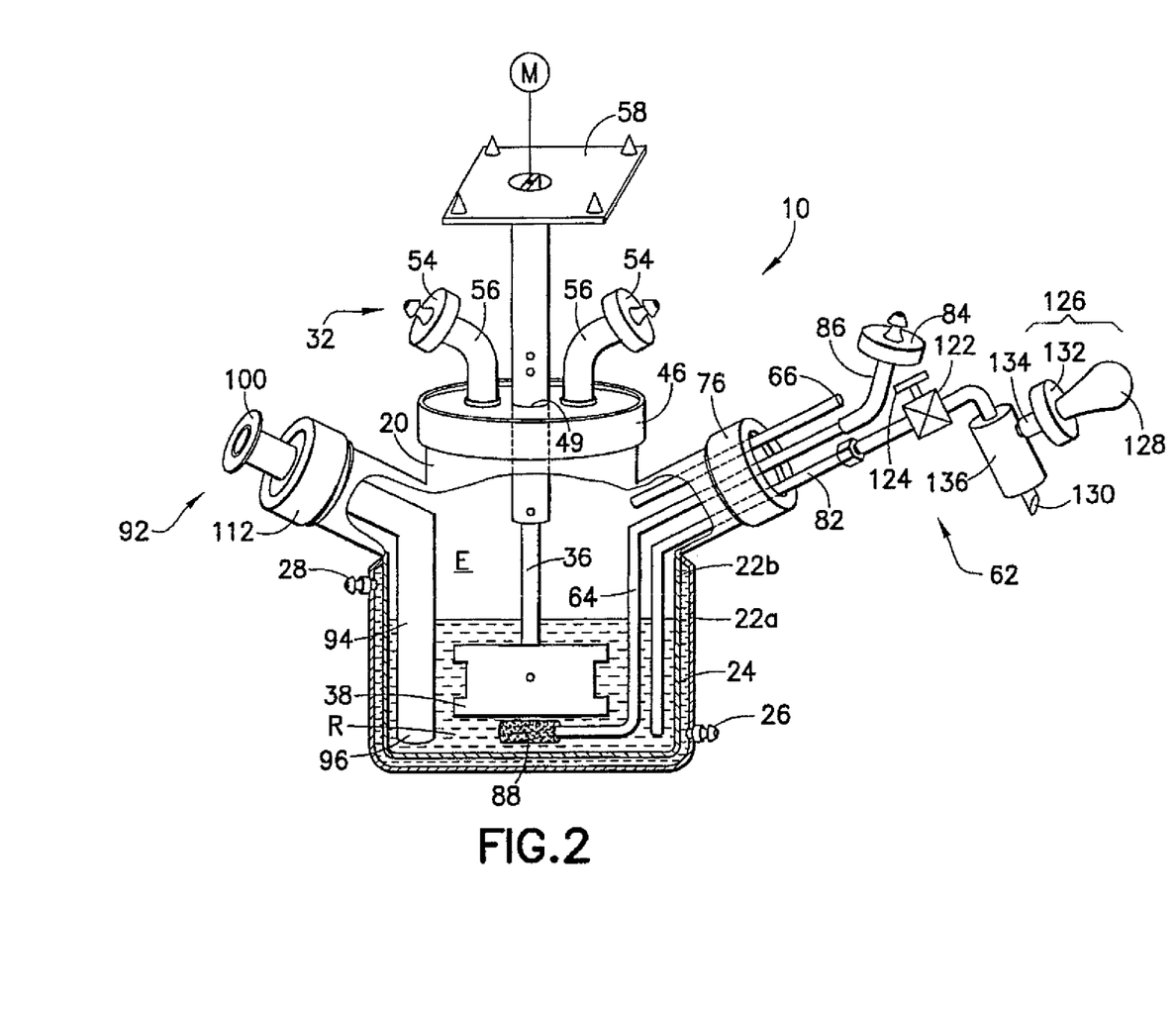
FIG. 2 is an assembled and partially perspective view of the bioreactor of FIG. 1.

Referring generally to FIGS. 1-2, an embodiment of a "seed" bioreactor 10 for performing biological and/or biochemical reactions is shown. Bioreactor 10 is generally defined by a reaction vessel 20 which is illustrated as having a cylindrical shape for exemplary purposes. Reaction vessel 20 is intended to encompass and retain a reaction medium R which is to undergo a biological and/or biochemical reaction. Accordingly, it is desirable that vessel 20 be made of a material that is inert to reaction medium R, for example, stainless steel or a suitably lined metallic vessel, or possibly an inert plastic material. This type of construction is desirable to prevent introducing unwanted substances into reaction medium R. Reaction vessel 20 is of a double-walled construction comprising an outer wall 22a and an inner wall 22b. Outer wall 22a and inner wall 22b define spacing therebetween for introduction of water thereby forming a water jacket 24 within the wall of reaction vessel 20. Water jacket acts as a temperature controlling device for maintaining/regulating the temperature of reaction medium R and, thus, reaction vessel 20 generally, for example, at a predetermined temperature. Water is typically used as the temperature controlling medium and is passed through water jacket 24 surrounding reaction vessel 20 and may be circulated at a constant temperature from a constant temperature bath, as an example.

Water jacket 24 has an inlet 26 and an outlet 28 for passing water therethrough to maintain the temperature of reaction medium R and reaction vessel 20. In the illustrated embodiment, inlet 26 of water jacket 24 may be positioned at a lower portion of outer wall 22a and outlet 28 may be positioned at an upper portion of outer wall 22a on the opposite side thereof. Accordingly, in order to provide a constant temperature to reaction vessel 20, both inlet 26 and outlet 28 are connected to a constant temperature bath via a circulation line (not shown) and a circulation pump (not shown). Water jacket 24 may be controlled so as to maintain constant temperature by temperature signals from some form of heat sensor connected to an external control unit (not shown) such as a computer. Conventional circulation connections between inlet 26 and outlet 28 of water jacket 24 may be used to create a closed loop system. If desired, inlet 26 may be positioned at an upper portion of outer wall 22a while outlet 28 is positioned at a lower portion to encourage the venting of air from water jacket 24 and to minimize incomplete filling of water jacket 24.

Reaction vessel 20 defines several ports or openings, including a mixing port 30, a reaction port 60, and a harvesting port 90. These ports 30, 60, 90 are covered by respective covering or closure devices which are discussed herein. These closure devices seal ports 30, 60, 90 to form an enclosed environment E or space within reaction vessel 20 suitable for biological and/or biochemical reactions. Mixing port 30 supports a mixing apparatus 32 which effectuates a generally fluid-tight seal with mixing port 30 to close mixing port 30 and, further, treatment of reaction medium R as discussed herein. Mixing apparatus 32 includes an agitator 34 which extends through mixing port 30 into reaction vessel 20. Agitator 34 comprises a shaft 36 extending into reaction vessel 20 and a paddle-shaped impeller 38 disposed in the enclosed environment E defined by reaction vessel 20 for stirring or agitating reaction medium R received in reaction vessel 20. Impeller 38 may take other conventional forms known within the bioreactor/fermenter art. Agitator 34 desirably extends into reaction vessel 20 to ensure sufficient agitation/stirring of reaction medium R when in operation and impeller 38 is sufficiently spaced from inner wall 22b of reaction vessel 20 to ensure that sufficient agitation/stirring/oxygen transfer rate of reaction medium R can occur. Agitator 34 is supported in a generally vertical or upright position by a mounting and sealing apparatus 40 engaged in mixing port 30. However, agitator 34 remains rotatable through mounting and sealing apparatus 40. Mounting and sealing apparatus 40 supports agitator 34 while maintaining a generally fluid-tight seal of mixing port 30 to prevent any contamination of reaction medium R in reaction vessel 20.

For driving agitator 34, a motor M or other driving device may be employed, typically outside of reaction vessel 20. Motor M may have any suitable transmission mechanism for transmitting driving power to agitator 34. Reaction medium R is mixed when the torque of motor M is transmitted to agitator shaft 36 and impeller 38 through the fluid-tight seal formed by mounting and sealing apparatus 40. Further, driving device (or motor M) may be actuated by a command signal from a control unit (not shown) to cause agitator 34 to rotate. By controlling the agitation condition in reaction vessel 20, it is possible to employ various states or speeds of agitation to assist in the reaction process of reaction medium R in reaction vessel 20.

Mounting and sealing apparatus 40 (hereinafter "mounting apparatus 40") comprises a sealing "first" cover 42 adapted to enclose and substantially seal mixing port 30. Cover 42 is adapted to engage or seat on/in mixing port 30 and, in particular, seal against a first rim 44 of reaction vessel 20 which defines mixing port 30. A gasket may also be used to ensure a generally fluid-tight characteristic between cover 42 and rim 44. Cover 42 is secured to reaction vessel 20 and on rim 44 in particular by a securing ring 46, thereby closing and substantially sealing mixing port 30. In one embodiment, ring 46 is internally threaded to engage an externally threaded portion 48 of reaction vessel 20 below rim 44. The threaded engagement between these elements secures the position of cover 42 on rim 44 and, further, the generally fluid-tight characteristic between cover 42 and rim 44. Agitator 34 extends through a central opening 49 in cover 42 and a generally fluid-tight seal is provided between agitator 34 and central opening 49. If desired, a nut head (not shown) or similar structure may be integrated or formed with the body of rim 44 to allow easy threaded engagement of rim 44 to externally threaded portion 48.

Cover 42 defines one or more vent openings 50 which accept vent structures or valves 52. Vent valves 52 may be threadedly engaged in vent openings 50 which allow venting of the enclosed environment E defined by reaction vessel 20. Vent valves 52 may be one-way valves that prevent external contamination from entering enclosed environment E. Additionally, filter elements 54 may be placed in fluid communication with and downstream of vent valves 52 and may be connected to vent valves 52 by tubing 56 to substantially prevent any contamination from reaction medium R from reaching the external atmosphere. Vent valves 52 may be used, for example, to ensure that reaction medium R in reaction vessel 20 is not compromised by an excess build-up of gasses introduced into reaction vessel 20. Finally, agitator 34 may be connected to an end or coupling plate 58 which is adapted for connection to the drive output of motor M for imparting rotational driving force to agitator 34 and agitator shaft 36 and impeller 38 in particular.

As indicated previously, reaction vessel 20 defines or includes reaction port 60. A reaction assembly 62 is inserted in reaction port 60 and effectuates a generally fluid-tight seal with reaction port 60 to close and seal reaction port 60. Reaction assembly 62 is provided as the interface device for introducing reaction medium R and reaction enabling materials and substances into reaction vessel 20, as well as for withdrawing or removing quantities of reaction medium R from reaction vessel 20 for sampling and testing purposes. Generally, reaction assembly 62 includes a gas introduction conduit 64, a reactant introduction conduit 66, and a sampling device 68. Reaction assembly 62 generally extends through reaction port 60 and into reaction vessel 20.

A sealing "second" cover 72 is provided as part of reaction assembly 62 and is used to enclose and substantially seal reaction port 60. Cover 72 is adapted to engage or seat on/in reaction port 60 and, in particular, seal against a second rim 74 of reaction vessel 20 which defines reaction port 60. Cover 72 is secured to reaction vessel 20 and on rim in particular by a "second" securing ring 76, thereby closing and substantially sealing reaction port 60. A gasket or O-ring G is provided between cover 72 and ring 76 to ensure a generally fluid-tight characteristic between cover 72 and rim 74. In one embodiment, ring 76 is internally threaded to engage an externally threaded portion 78 of reaction vessel 20 below (i.e., adjacent) rim 74. The threaded engagement between these elements secures the position of cover 72 on rim 74 and, further, the generally fluid-tight characteristic between cover 72 and rim 74. Although the mixing and reaction ports 30, 60 are shown with respective covers 42, 72 threadably secured to reaction vessel rims 44, 74 to establish a generally fluid-tight construction, it is also possible to permanently affix the respective covers 42, 72 to reaction vessel rims 44, 74. Cover 72 defines several openings 80 for passage of gas introduction conduit 64, introduction conduit 66, and a collection conduit 82 associated with sampling device 68. Conduits 64, 66, 82 are each disposed in the respective openings 80 in a generally fluid-tight manner. If desired, a nut head (not shown) or similar structure may be integrated or formed with the body of rim 74 to allow easy threaded engagement of rim 74 to externally threaded portion 78.

Further, a filter element 84 may be associated with gas introduction conduit 64 via tubing 86 so that sterile-filtered gas may be introduced in reaction medium R by the gas introduction conduit 64 and to prevent any contamination from reaching reaction medium R from the external gas supply source (not shown). Gas introduction conduit 64 is adapted to introduce gas, for example, oxygen or air, into reaction medium R in reaction vessel 20 to assist in the biochemical process occurring in the reaction medium R. For example, if reaction medium R contains cells for culturing, oxygen is necessary for cell growth and oxygen or air may be introduced via gas introduction conduit 64 to support the cell growth. Further, the introduction of carbon dioxide may be necessary to form essential ions for growing cells and is another example of a gas that may be introduced into reaction medium R via gas introduction conduit 64. Because reaction vessel 20 is designed to maintain a generally fluid-tight and sealed condition, an anaerobic gas may alternatively or additionally be introduced into reaction medium R and may be used to aerate reaction medium R. Gas introduction conduit 64 may be connected to a gas bomb (not shown), for example, as a gas supply source for the gas introduction conduit 64 and a metering or control valve may be associated with gas introduction 64 to control the delivery of gas into reaction medium R. Finally, a sparger 88 is disposed at the end of gas introduction conduit 64 for distributing gas into reaction medium R and, desirably, to reduce size of the gas bubbles introduced into the reaction medium R to prevent damage to cells or other bio-matter in the reaction medium R. Although sparger 88 is illustrated in the figures for distributing the introduced gas into reaction medium R, other equivalent means for introducing, distributing, and/or aerating gas into reaction medium R and enclosed environment E generally may be substituted in place of sparger 88. Examples of such equivalent devices include devices capable of caged sparging, medium perfusion, membrane diffusion, etc.

As indicated previously, reaction vessel 20 defines or includes harvesting port 90. A harvesting outlet assembly (hereinafter "harvesting outlet 92") is inserted into and disposed in harvesting port 90 and is used to "harvest" or withdraw reaction medium R from reaction vessel 20, typically in large volumes, and transfer the same to one or more larger bioreactor vessels for further culturing/fermentation (i.e., scale-up processing). Harvesting outlet 92 includes a harvesting conduit 94 which is inserted through harvesting port 90 and extends into reaction vessel 20 to be in contact with reaction medium R in enclosed environment E defined by reaction vessel 20 for removing all or a portion of the reaction medium R to a downstream process. A first or internal end 96 of harvesting conduit 94 is disposed in reaction vessel 20 and is in contact with reaction medium R in reaction vessel 20. A second or external end 98 of harvesting conduit 94 desirably terminates in a generally planar sanitary coupling 100 of conventional design. The function and use of sanitary coupling 100 is discussed herein.

Harvesting outlet 92 is desirably adapted to effectuate a generally fluid-tight seal with harvesting port 90 to close and seal harvesting port 90. Harvesting outlet 92 comprises a sealing "third" cover 102 disposed about harvesting conduit 94, or affixed thereto, and which extends radially outward from harvesting conduit 94. Cover 102 is used to engage and/or seat on/in harvesting port 90 and, in particular, seal against a third rim 104 of reaction vessel 20 defining the harvesting port 90. Cover 102 is then secured to reaction vessel 20 and on rim 104 in particular by a "third" securing ring 112, thereby enclosing and substantially sealing the harvesting port 90. Accordingly, in one embodiment, ring 112 may be an annular structure that is internally threaded and rotatably received about harvesting conduit 94 on externally threaded portion 108 below (i.e., adjacent) rim 104. A gasket or O-ring 106 is provided between ring 112 and rim 104 to ensure a generally fluid-tight characteristic between cover 102 and rim 104. Thus, ring 112 is similar in structure and operation to rings 46, 76 discussed previously. While a threaded engagement between rim 112 and externally threaded portion 108 is shown in the figures, it is also possible to permanently affix ring 112 to reaction vessel rim 104. If desired, a nut head (not shown) or similar structure may be integrated or formed with the body of rim 112 to allow easy threaded engagement of rim 112 to externally threaded portion 108.

As indicated previously, harvesting conduit 94 may terminate at external end 98 with sanitary coupling 100 which may be used to connect harvesting outlet 92 with another vessel or an apparatus used to remove all or a portion of reaction medium R from reaction vessel 20. Harvesting conduit 94 (and sanitary coupling 100) may alternatively be sealed and/or covered (not shown) to prevent contamination of the enclosed environment E of the reaction vessel 20. Sanitary coupling 100 may also be connected to a sanitary valve 110 via a sanitary clamp (not shown) or other suitable union. Sanitary valve 110 allows metered or controlled withdrawal of reaction medium R from reaction vessel 20 and comprises a valve body 114 and an actuator 116 or control associated with valve body 114. Actuator 116 controls operation of valve body 114, for example, by opening and closing valve body 114 to permit the controlled withdrawal of reaction medium R from reaction vessel 20. Valve body 114 desirably itself includes sanitary inlet and outlet couplings 118, 120 for engaging the sanitary coupling 100 at external end 98 of harvesting conduit 94 and a downstream apparatus to which the reaction medium R is to be supplied such as a larger bioreactor vessel for continued processing of the reaction medium R as discussed herein in connection with FIG. 3.

For supplying reaction vessel 20 with reactants which form and/or promote culturing/fermentation of reaction medium R, reaction assembly 62 includes introduction conduit 66. Introduction conduit 66 is positioned to extend outward from ring 76 and is typically connected to a reactant source for supplying reactants which form and/or promote culturing/fermentation of reaction medium R. However, in the event introduction conduit 66 is not connected to a reactant source in some manner, the introduction conduit 66 may be sealed and/or covered (not shown) to prevent contamination of the enclosed environment E of the reaction vessel 20. Introduction conduit 66 may include a similar sanitary coupling (not shown) to sanitary coupling 100 which may cover introduction conduit 66 in the manner discussed previously so that reactants may be provided to reaction vessel 20 without contamination. Further, reactants could be introduced automatically from, for example, a hopper (not shown) connected to introduction conduit 66. If desired, reactants may be introduced to reaction vessel 20 at a constant rate by dosing a predetermined amount of the desired reactants at desired time intervals via a feed pump (not shown) connected to introduction conduit 66.

As discussed previously, one component of reaction assembly 62 is sampling device 68. Sampling device 68 is provided for removing a portion, typically a small amount of reaction medium R from reaction vessel 20, for testing purposes to monitor the culturing/fermentation process for completeness or determine whether additions to reaction medium R are needed to complete the process. Sampling device 68 generally includes collection conduit 82, discussed previously, which extends through reaction port 60 and into reaction vessel 20 to a position in fluid contact with reaction medium R. A sampling valve 122 is positioned outside of reaction vessel 20 and is provided in collection conduit 82 for controlling the outtake of reaction medium R from reaction vessel 20 and to maintain a sterile barrier of reaction medium R with the external environment. A valve actuator 124 is provided to control operation of sampling valve 122. As an example, sampling valve 122 may be a cavity filled ball valve or diaphragm valve, although any number of other types of aseptic valves may be implemented in various embodiments depending upon the application for which sampling device 68 is to be employed.

A sample extractor 126 is in fluid communication with sampling valve 122 provided in collection conduit 82. Sample extractor 126 is located downstream of sampling valve 122 and exterior to the reaction vessel 20. Sampling valve 122 and sample extractor 126 are operable to permit a user of bioreactor 10 to selectively remove a small amount of reaction medium R from reaction vessel 20 for testing and evaluation purposes or other purposes as desired. Sample extractor 126 includes a vacuum generating portion 128, such as a simple vacuum bulb, which is in fluid communication with collection conduit 82 for producing vacuum (i.e., negative) pressure within collection conduit 82 to cause removal of a small sample of reaction medium R from reaction vessel 20 when sampling valve 122 is in an open position. Sampling device 68 allows removal of a small amount of reaction medium R when sampling valve 122 in an open position without contaminating the remaining reaction medium R within reaction vessel 20, as described herein. Collection conduit 82 terminates in a discharge outlet 130 from which the withdrawn sample is extracted to another vessel or container. Discharge outlet 130 may be a simple beveled orifice as shown or could include an on-off valve for controlling flow of the sampled reaction medium R or terminating such flow. A filter element 132 is desirably disposed between vacuum generating portion 128 and a port 133 on collection conduit 82 which connects the collection conduit 82 to vacuum generating portion 128 to prevent or reduce the possibility of introducing contamination to reaction medium R when sampling valve 122 is in an open state. Conventional tubing 134 is used to complete the fluid connection between filter element 132 and port 133. A sampling housing 136 may be provided around the discharge end or portion of collection conduit 82 upstream of discharge outlet 130 and is provided, for example, to guide the user in connecting a collection container or vessel to discharge outlet 130.

In operation, a collection container or vessel (not shown) is placed in fluid connection with discharge outlet 130. A vacuum is created by forcing air out of the sampling housing 136, which is in fluid communication with collection conduit 82 and the collection container. A seal is formed, typically in a generally fluid-tight or sealed manner. Sampling valve 122 is opened and sample extractor 126 is opened and the vacuum generated in the collection conduit 82, the collection container and vacuum generating portion 128 is released by drawing reaction medium R through sampling valve 122 and collection conduit 82 and ultimately into the collection container. Thus, sample extractor 126 creates vacuum pressure in collection conduit 82 which withdraws a sample of reaction medium R from reaction vessel 20 and delivers this sample to discharge outlet 130 and, further, the collection container or vessel connected thereto. Sampling valve 122 may then be operated to a closed position re-closing collection conduit 82 and again sealing the enclosed environment E in reaction vessel 20. A sample of reaction medium R is now deposited within the collection container and this container may be removed for testing and evaluation of the collected sample of reaction medium R.

In order to further enhance the ability to obtain a sterile sample, the portion of the sampling device 68 downstream of sampling valve 122 (i.e., sample extractor 126) may be removable/replaceable. Thus, sample extractor 126 can be removed from sampling valve 122 and cleaned with alcohol or other sterilizing medium to ensure cleanliness outside valve 122. Alternatively, another sterile portion of sampling device 68 may be affixed to sampling valve 122 to reduce the possibility for contaminating subsequent samples of reaction medium R taken from reaction vessel 20. The detachability of this downstream portion may be accomplished in a number of ways including threaded engagement, snap fit, and like simple mechanical connection techniques.

Figure 3:
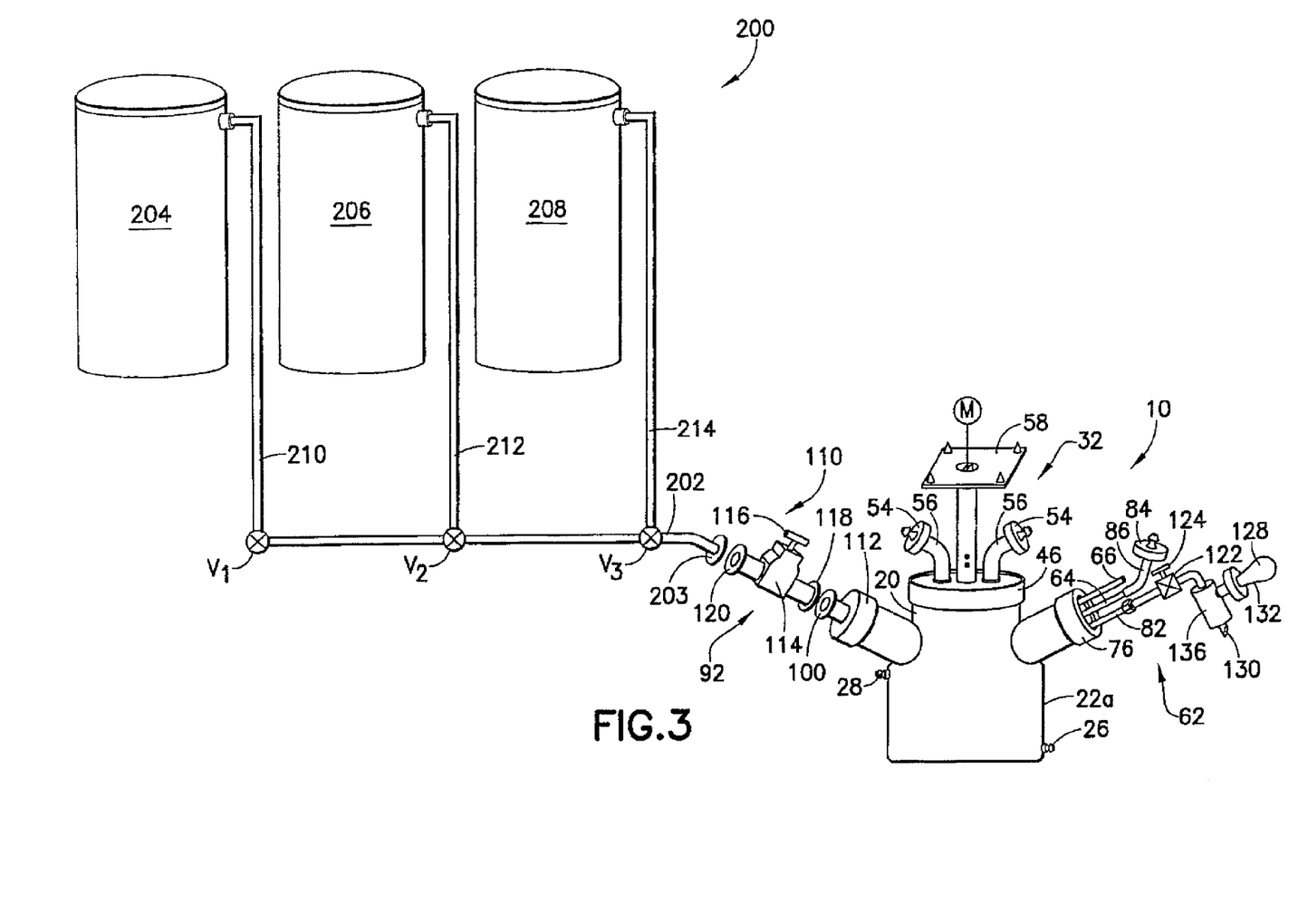
FIG. 3 is a schematic diagram showing the bioreactor of FIG. 2 as part of a system wherein the bioreactor is a seed bioreactor for larger bioreactor devices.

Referring further to FIG. 3 a bioreactor system 200 comprising bioreactor 10 as a "seed" bioreactor for larger processing vessels is shown. As is known in the medical art, bioreactors are often used for initial culturing/fermentation of biological and biochemical substances, which are then transferred to larger processing vessels for scale-up processing once an effective amount of processed material is present in the "seed" bioreactor for transfer to the larger vessel. FIG. 3 illustrates such a system 200 comprising bioreactor 10 which is connected by harvesting sanitary valve 110 to an input/introduction line or conduit 202 of the system 200. Input line 202 typically includes a sanitary coupling 203 similar to sanitary coupling 120 on sanitary valve 110 and which is connected to sanitary coupling 120 by a sanitary clamp (not shown) or other suitable union. This sanitary coupling 203 on input line 202 forms the "input port" to input line 202. The union for effecting a sanitary connection between couplings 120, 230 is typically similar to the union between sanitary coupling 100 on harvesting conduit 94 and inlet sanitary coupling 118 on sanitary valve 110. Input line 202 is connected to several large or scale-up bioreactor devices, or main bioreactors 204, 206, 208, via respective main bioreactor input lines 210, 212, 214 and control valves $V_1$, $V_2$, $V_3$. As indicated, main bioreactors 204, 206, 208 provide for performing biological and/or biochemical reactions on a larger scale than "seed" bioreactor 10 as is common in scale-up processes.

Bioreactor 10 is generally assembled as discussed hereinafter. However the following assembly steps are intended merely as an example of one possible assembly method for bioreactor 10. Bioreactor 10 is intended to provide a sterile and sealed enclosed environment for reaction medium R in reaction vessel 20. Accordingly, the mixing port 30, reaction port 60, and harvesting port 90 are each be sealed and sterilized via heat, chemical or other method before the reaction medium R can be aseptically introduced into reaction vessel 20 through a sterilizing grade liquid filter (not shown). Alternatively, if reaction medium R can withstand sterilization via heat, chemical or radiation, reaction medium R can be introduced into the vessel 20 and sealed prior to total vessel sterilization. Beginning with mixing port 30, mixing apparatus 32 is inserted into mixing port 30 with mounting and sealing apparatus 40 enclosing and sealing the mixing port 30. Agitator 34 may be preassembled with cover 42, and cover 42 may have vent valves 52 secured in openings 50. Likewise, ring 46 may be disposed about agitator 34 so that the agitator 34, cover 42, and ring 46 are in a preassembled state. This preassembled structure is inserted into mixing port 30 and ring 46 is secured to threaded portion 48 below rim 44, which defines mixing port 30, to complete the assembly of mixing apparatus 32 in mixing port 30.

Next, reaction assembly 62 may be inserted into reaction port 60 to enclose and seal the reaction port 60. Ideally, reaction assembly 68 is preassembled with cover 72 supporting conduits 64, 66, 82 and ring 76 disposed about conduits 64, 66, 82. Sampling device 68 may be preassembled or connected to collection conduit 82. This entire preassembled structure is then inserted into reaction port 60 and ring 76 is secured to threaded portion 78 below rim 74, which defines reaction port 60, to complete the assembly of reaction assembly 62 in reaction port 60.

Finally, harvesting outlet 92 may be inserted in harvesting port 90 to enclose and seal the harvesting port 90. As with the mixing apparatus 32 and reaction assembly 62 discussed previously, harvesting outlet 92 is desirably preassembled, typically with sanitary valve 110 connected to the harvesting outlet 92 so that the entire harvesting outlet 92 and sanitary valve 110 structure may be inserted into harvesting port 90. Cover 102 associated with harvesting outlet 92 is secured to threaded portion 108 below rim 104, which defines harvesting port 90, to complete the assembly of harvesting outlet 92 in harvesting port 90.

With bioreactor 10 now assembled, reaction medium R may be introduced into reaction vessel 20 to accomplish the intended biological and/or biochemical reaction. The vessel 20 may be pre-sterilized by the above-mentioned techniques while empty, and reaction medium R may be aseptically introduced through a sterilizing grade filter, or reaction medium R can be sterilized via above-described methods if the reaction medium R can withstand the sterilization process. Reaction vessel 20 may be maintained at a predetermined temperature by operation of water jacket 24. The intended biological and/or biochemical reaction may be carried out in reaction vessel 20 in the presence of one or more microorganisms or one or more chemical substances such as, for example, enzymes, under agitation/stirring action of agitator 34. Through rotation of reaction medium R in reaction vessel 20, the reaction medium R is treated to effect dispersion and mixing of constituent reactants/substances. In addition, reaction medium R may be further aerated through gas introduction conduit 64 which may be necessary for cell growth, as discussed previously. At various intervals during processing, samples of reaction medium R may be taken to monitor the processing of the reaction medium R. Such sampling of reaction medium R was detailed previously. Additional substances, such as essential nutrients to support cultivation, may be introduced to reaction medium R through introduction conduit 66 which is part of the reaction assembly 62. Once it is determined that reaction medium R is ready for further processing, the reaction medium R may be transferred to scale-up processing in system 200, which includes several scale-up vessels or main bioreactors 204, 206, 208. The transfer of reaction medium R is accomplished through harvesting sanitary valve 110, for example, with the aid of a transfer pump (not shown) in input line 202. Sterile addition lines and harvest lines should be connected aseptically by using alcohol or other sterilizing grade chemical to minimize contamination. The tubing used to transfer the reaction medium R to main bioreactors 204, 206, 208 should also be pre-sterilized via methods described previously to minimize introduction of contaminants during the transfer process.

It may also be preferable to control operation of "seed" bioreactor 10, including agitator 34 and water jacket 24, and the introduction of the reactants and gas to reaction medium R, via a control unit (not shown) such as a computer. In addition, reactant medium R may be removed under the control of the control unit to transfer the reaction medium R to one or more of main bioreactors 204, 206, 208. For example, in the case of control of water jacket 24, the control unit may receive temperature input data from temperature sensors in reaction vessel 20 and may adjust operation of water jacket 24 to control the temperature within reaction vessel 20 within a prescribed temperature range. Similarly, the control unit may control the fixed delivery of reactant material to reaction vessel 20 by controlling a feed pump connected to introduction conduit 66 associated with reaction assembly 62. Further, the control unit could also control the supply of gas from a gas bomb connected to gas introduction conduit 64, for example, by controlling a control valve disposed between the gas bomb and gas introduction conduit 64. Still further, the control unit could also control the supply of acid/base, gas, nutrients, etc. through the use of an internal measuring device monitoring the parameter to be controlled.

While the present invention was described by way of a detailed description of several embodiments of a fluid injection apparatus and adaptor pump therefor, those skilled in the art may make modifications and alterations to this invention without departing from the scope and spirit of the invention. Accordingly, the foregoing description is intended to be illustrative rather than restrictive. The invention described hereinabove is defined by the appended claims, and all changes to the invention that fall within the meaning and the range of equivalency of the claims are to be embraced within their scope.

The invention claimed is:

1. A bioreactor apparatus for performing biological and biochemical reactions comprising:
   a vessel comprising at least three separate and distinct ports, the ports comprising a mixing port, a reaction port, and a harvesting port;
   an agitator extending through the mixing port into the vessel;
   a reaction assembly extending through the reaction port into the vessel, the reaction assembly consists of:
   a) a gas conduit adapted to introduce gas into a reaction medium in the vessel;
   b) a sampling device adapted to remove a portion of the reaction medium from the vessel without contamination of the remaining reaction medium remaining in the vessel, wherein the sampling device consists of:
   i) a collection conduit extending into the vessel;
   ii) a sampling valve positioned in the collection conduit and disposed outside the vessel; and
   iii) an extractor associated with the collection conduit and disposed outside of the vessel and adapted to remove a sample portion of the reaction medium through the collection conduit; and
   c) an introduction conduit permitting the introduction of at least the reaction medium into the vessel,
   wherein the gas conduit, sampling device and introduction conduit have a unitary common support;
   wherein the unitary common support is removeably fixed to the reaction port such that the reaction assembly is placed in and removed from the reaction port as a unit;
   wherein the harvesting port consists of a dedicated harvesting outlet extending therethrough for the withdrawal of the reaction medium from the vessel, the dedicated harvesting outlet configured to be coupled to another vessel via a sanitary coupling.

2. The bioreactor apparatus of claim 1, wherein the bioreactor further comprises a water jacket adapted to regulate the temperature of the reaction medium.

3. The bioreactor apparatus of claim 1, wherein the gas conduit includes a sparger coupled to the gas conduit to aerate the reaction medium.

4. The bioreactor apparatus of claim 1, wherein the agitator extends through a cover sealing the mixing port.

5. The bioreactor apparatus of claim 1, wherein the agitator is coupled to an external drive device.

6. The bioreactor apparatus of claim 5, wherein the external drive device includes a motor.

7. The bioreactor apparatus of claim 3, wherein the gas is introduced as bubbles and the sparger coupled to the gas conduit of the reaction assembly is configured to limits the size of the bubbles introduced into the vessel.

8. The bioreactor apparatus of claim 1, wherein the collection conduit includes a discharge outlet for releasing the sample portion of the reaction medium from the collection conduit without contamination of the remaining reaction medium.

9. The bioreactor apparatus of claim 8, wherein the extractor includes:
   a vacuum generating portion adapted to decrease pressurization in the collection conduit; and
   a filter element provided fluidly between the vacuum generating portion and the collection conduit.

10. A bioreactor system for performing biological and biochemical reactions comprising:
   a seed bioreactor comprising:
      a vessel comprising at least three separate and distinct ports, the ports comprising a mixing port, a reaction port, and a dedicated harvesting port;
      an agitator extending through the mixing port into the vessel; and
      a reaction assembly extending through the reaction port into the vessel, the reaction assembly consisting of:
         1) a gas conduit adapted to introduce gas into a reaction medium in the vessel;
         2) a sampling device adapted to remove a sample portion of the reaction medium from the vessel without contamination of the remaining reaction medium, wherein the sampling device consisting of:
            i) a collection conduit extending into the vessel;
            ii) a sampling valve positioned in the collection conduit outside the vessel; and
            iii) an extractor associated with the collection conduit outside of the vessel and adapted to remove a sample portion of the reaction medium through the collection conduit;
         3) an introduction conduit permitting the introduction of at least the reaction medium into the vessel,
      wherein the gas conduit, sampling device and introduction conduit of the reaction assembly have a unitary common support;
      wherein the unitary common support is removeably fixed to the reaction port so that the reaction assembly is placed in and removed from the reaction port as a unit;
      wherein the dedicated harvesting port consists of a dedicated harvesting outlet extending therethrough for the withdrawal of the reaction medium from the seed bioreactor via the dedicated harvesting port; and
   a main bioreactor adapted to perform biological and biochemical reactions and adapted to be placed in fluid communication with the vessel via the dedicated harvesting outlet wherein the dedicated harvesting outlet is coupled to the main bioreactor via a sanitary coupling to provide reaction medium withdrawn from the seed bioreactor to the main bioreactor.

11. The bioreactor system of claim 10, wherein the seed bioreactor further comprises a water jacket adapted to regulate the temperature of the reaction medium.

12. The bioreactor system of claim 10, wherein the agitator extends through a cover sealing the mixing port.

13. The bioreactor system of claim 10, wherein the agitator is coupled to an external drive device.

14. The bioreactor system of claim 10, wherein the gas is introduced as bubbles; and wherein the bioreactor system further comprises a sparger coupled to the gas conduit and configured to limit the size of the bubbles introduced into the vessel.

15. The bioreactor system of claim 10, wherein the extractor further includes: a vacuum generating portion adapted to decrease pressurization in the collection conduit; and a filter element provided fluidly between the vacuum generating portion and the collection conduit.

16. The apparatus bioreactor system of claim 11, wherein the dedicated harvesting outlet extends through a cover sealing the dedicated harvesting port and allowing passage of the dedicated harvesting outlet therethrough.

17. The bioreactor system of claim 10, wherein the main bioreactor comprises an inlet port, and wherein the main bioreactor is placed in fluid communication with the vessel via the sanitary coupling which is between the dedicated harvesting outlet and the inlet port.

* * * * *